US006986747B2

(12) United States Patent
McCulloch et al.

(10) Patent No.: US 6,986,747 B2
(45) Date of Patent: Jan. 17, 2006

(54) METHOD OF MEASURING THE STRESS OR RELAXATION LEVEL OF A MAMMAL

(75) Inventors: Laura McCulloch, Hampshire (GB); Benjamin Wiegand, Newtown, PA (US); Kathryn Dean, Ringoes, NJ (US); Neena Tierney, Yardley, PA (US); Nikiforos Kollias, Skillman, NJ (US)

(73) Assignee: Johnson & Johnson Consumer Companies, Skillman, NJ (US)

( * ) Notice: Subject to any disclaimer, the term of this patent is extended or adjusted under 35 U.S.C. 154(b) by 320 days.

(21) Appl. No.: 10/353,525

(22) Filed: Jan. 29, 2003

(65) Prior Publication Data

US 2003/0220550 A1 Nov. 27, 2003

(51) Int. Cl.
*A61B 5/00* (2006.01)
*A61M 21/00* (2006.01)

(52) U.S. Cl. ............... 600/558; 600/559; 600/26
(58) Field of Classification Search ................. 600/310, 600/322, 323, 336, 552–555, 557–559, 26–28
See application file for complete search history.

(56) References Cited

U.S. PATENT DOCUMENTS

| | | | |
|---|---|---|---|
| 4,013,417 A | 3/1977 | Raffaele |
| 4,375,421 A | 3/1983 | Rubin et al. |
| 4,556,557 A | 12/1985 | Reichert |
| 4,657,690 A | 4/1987 | Grollier et al. |
| 4,664,835 A | 5/1987 | Grollier et al. |
| 4,668,513 A | 5/1987 | Reichert |
| 4,670,264 A | 6/1987 | Warren et al. |
| 4,671,959 A | 6/1987 | Warren et al. |
| 4,877,322 A | 10/1989 | Hill |
| 5,009,813 A | 4/1991 | Watanabe et al. |
| 5,079,227 A | 1/1992 | Handjani et al. |
| 5,083,062 A | 1/1992 | Ichihara |
| 5,124,078 A | 6/1992 | Baust |
| 5,275,761 A | 1/1994 | Bergmann |
| 5,284,603 A | 2/1994 | Repinec, Jr. et al. |
| 5,304,112 A | 4/1994 | Mrklas et al. |
| 5,350,774 A | 9/1994 | Palou |
| 5,403,263 A | 4/1995 | Rodgers |
| 5,403,587 A | 4/1995 | McCue et al. |
| 5,466,446 A | 11/1995 | Stiefel et al. |
| 5,497,771 A | 3/1996 | Rosenheimer |
| 5,540,853 A | 7/1996 | Trinh et al. |
| 5,578,312 A | 11/1996 | Parrinello |
| 5,597,406 A | 1/1997 | Fischer et al. |
| 5,597,407 A | 1/1997 | Fischer et al. |
| 5,607,980 A | 3/1997 | McAtee et al. |
| 5,614,553 A | 3/1997 | Ashmead et al. |
| 5,711,899 A | 1/1998 | Kawa et al. |
| 5,716,919 A | 2/1998 | Sano |
| 5,753,637 A | 5/1998 | Fried |

(Continued)

FOREIGN PATENT DOCUMENTS

| | | |
|---|---|---|
| AU | 579191 | 4/1986 |
| AU | 654850 | 5/1992 |
| AU | 664987 | 10/1992 |
| AU | 701232 | 12/1995 |
| AU | 723030 | 5/1996 |
| AU | 43839 | 5/1998 |
| AU | 730992 | 5/1998 |
| AU | 60334/98 | 8/1998 |
| CA | 2 153 313 | 8/1994 |
| CA | 2 155 766 | 8/1994 |
| CA | 2 127 348 | 1/1995 |
| CA | 2 127 657 | 1/1995 |
| CA | 2 167 174 | 1/1995 |
| CA | 2 216 964 | 10/1996 |
| CA | 2247825 | 2/1997 |
| CA | 2244887 | 8/1997 |
| DE | 3445547 A1 | 7/1985 |
| DE | 199 52970 A1 | 5/2001 |
| EP | 0 881 832 A2 | 11/1995 |
| EP | 0 713 860 B1 | 5/1996 |
| EP | 0 841 061 A2 | 5/1998 |
| EP | 978273 | 2/2000 |

(Continued)

OTHER PUBLICATIONS

"Biology of Beauty" article (pre Oct. 1999).
"Aromachology, the Science Behind the Fragrance" article (pre Oct. 1999).
Tube for Origins Diaper Service™ Balm (available before Oct. 1999).
Tube for Origins Love Me Tender™ lotion (available before Oct. 1999).
Tube for Origins Bare Hugs™ cream (available before Oct. 1999).
Bottle for Origins Baby Shower™ wash (available before Oct. 1999).
Package for Origins Short Cake™ bar (available before Oct. 1999).
Package for Origins Smooth Baby™ oil (available before Oct. 1999).
William J. Cunliffe, Acne, 1989, 1–11, Martin Dunitz Ltd., UK.

(Continued)

*Primary Examiner*—Eric F. Winakur

(57) ABSTRACT

A method of measuring the stress or relaxation level of a mammal and a method of measuring the activity of the sympathetic nervous system of a mammal by measuring quantititative levels of deoxyhemoglobin and oxyhemoglobin are disclosed. Preferably, the levels of deoxyhemoglobin and hemoglobin are measured by a noninvasive technique, such as spectroscopy. A method of changing the activity of the sympathetic nervous system of a mammal is also disclosed, wherein the method includes a step of administering an effective amount of sensory regimen to the mammal. The method is useful for humans who are operating vehicles or machinery, who are suffering from cardiovascular disease or related complications, who are pregnant, or who are preparing for sleep. In addition, a method of improving the complexion of the skin of a mammal is disclosed.

20 Claims, No Drawings

U.S. PATENT DOCUMENTS

| | | |
|---|---|---|
| 5,771,261 A | 6/1998 | Anbar |
| 5,789,953 A | 8/1998 | Au et al. |
| 5,792,739 A | 8/1998 | He et al. |
| 5,804,538 A | 9/1998 | Wei et al. |
| 5,849,310 A | 12/1998 | Trinh et al. |
| 5,855,884 A | 1/1999 | Theoharides |
| 5,871,757 A | 2/1999 | Cloughley et al. |
| 5,904,916 A | 5/1999 | Hirsch |
| 5,910,477 A | 6/1999 | Gordon |
| 5,916,576 A | 6/1999 | Dornoff et al. |
| 5,922,331 A | 7/1999 | Mausner |
| 5,958,462 A | 9/1999 | McLean |
| 5,965,502 A | 10/1999 | Balzer |
| 5,980,925 A | 11/1999 | Jampani et al. |
| 5,995,857 A * | 11/1999 | Toomim et al. ............ 600/340 |
| 6,134,460 A | 10/2000 | Chance |
| 6,245,769 B1 | 6/2001 | Arvanitis et al. |
| 6,416,481 B2 * | 7/2002 | Faubert et al. ............... 600/558 |
| 6,547,746 B1 * | 4/2003 | Marino ........................ 600/554 |
| 6,635,263 B2 | 10/2003 | Tanida et al. |
| 2002/0111529 A1 | 8/2002 | Licht |
| 2002/0151527 A1 | 10/2002 | Wiegand et al. |
| 2003/0005409 A1 | 1/2003 | Shoji et al. |
| 2003/0225095 A1 | 12/2003 | Wiegnand et al. |
| 2004/0175438 A1 | 9/2004 | Wiegand et al. |

FOREIGN PATENT DOCUMENTS

| | | |
|---|---|---|
| EP | 0 983 990 | 3/2000 |
| EP | 1198995 A1 | 4/2000 |
| EP | 1 082 960 A2 | 3/2001 |
| FR | 2191878 | 2/1974 |
| FR | 2730634 A1 | 8/1996 |
| JP | 3284619 | 11/1991 |
| JP | 2973368 | 12/1991 |
| JP | 4077416 | 3/1992 |
| JP | 2548074 | 6/1994 |
| JP | 1972802 | 12/1994 |
| JP | 06-104621 | 12/1994 |
| JP | 9227399 A | 2/1996 |
| JP | 9227400 A | 9/1997 |
| JP | 11-019076 | 1/1999 |
| JP | 11 023579 A | 1/1999 |
| JP | 11-34688 A | 2/1999 |
| JP | 2000 275248 A | 10/2000 |
| WO | WO 94/07461 | 4/1994 |
| WO | WO 96/12468 A1 | 5/1996 |
| WO | WO 96/25389 | 8/1996 |
| WO | WO 97/03646 | 2/1997 |
| WO | WO 97/28785 A1 | 8/1997 |
| WO | WO 97/30688 | 8/1997 |
| WO | WO 97/32560 A1 | 9/1997 |
| WO | WO 98/08846 A1 | 3/1998 |
| WO | WO 98/13022 | 4/1998 |
| WO | WO 98/27938 | 7/1998 |
| WO | WO 98/38973 | 9/1998 |
| WO | WO 99/09947 | 3/1999 |
| WO | WO 99/31511 A | 6/1999 |
| WO | WO 99/44577 | 9/1999 |
| WO | WO 99/63883 A | 12/1999 |
| WO | WO 00/01360 | 1/2000 |
| WO | WO 01/24807 A | 4/2001 |
| WO | WO 01/98442 A | 12/2001 |
| WO | WO 02/49600 A1 | 6/2002 |
| WO | WO 02/49629 A2 | 6/2002 |
| WO | WO 02/82198 A2 | 10/2002 |

OTHER PUBLICATIONS

S. Cohen, T. Kamarck, R. Mermelstein, A Global Measure of Perceived Stress, Journal of Health and Social Behavior 1983, 385–396, vol. 24 (Dec.).

P. Brantley, C. Waggoner, G. Jones, N. Rappaport, A Daily Stress Inventory: Development, Reliability, and Validity, Journal of Behavioral Medicine, 1987: 61–75, vol. 10, No. 1.

T.R. Cooper, H.R. Trunkfield, A.J. Zanella, W.D. Booth, An enzyme–linked Immunosorbent Assay for Cortisol in the Saliva of Man and Domestic Farm Animals, Journal of Endocrinology (1989) R13–R16.

A. Beck, G. Brown, N. Epstein, R. Steer, An inventory for Measuring Clinical Anxiety: Psychometric Properties, Journal of Consulting and Clinical Psychology, 1988, 893–897, vol. 56, No. 6.

A. Buske–Kirschbaum, S. Jobst, A Wustmans, C. Kirschbaum, W. Rauh, D. Hellhammer, Attenuated Free Cortisol Response to Psychosocial Stress in Children with Atopic Dermatitis, Psychosomatic Medicine, 1997:419–426, vol. 59.

A. Slominski, J. Wortsman, T. Luger, R. Paus, S. Solomon, Corticotropin Releasing Hormone and Proopiomelanocortin Involvement in the Cutaneous Response to Stress, Physiological Reviews, Jul. 2000:979–1020,vol.80, No. 3.

M. Morohashi, M. Toyada, Y. Luo, S. Higaki, Cutaneous Neurologic Factors are Involved in the Pathogenesis of Acne, The Journal of Investigative Dermatology: 820.,2000, vol. 114 (Abstract).

E. Aardal, A. Charlotte Holm, Cortisol in Saliva–Reference Ranges and Relation to Cortisol in Serum, European Journal Clin Chem, Clin Biochem 1995: 927–932, 33(No. 12).

D. Watson, L. Clark, A. Tellegen, Development and Validation of Brief Measures of Positive and Negative Affect: The PANAS Scales, Journal of Personality and Social Psychology, 1988:1063–1070, vol. 54, No. 6.

O. Wolkowitz, V. Reus, A. Keebler, N. Nelson, M. Friedland, L. Brizendine, E. Roberts, Double–Blind Treatment of Major Depression with Dehydroepiandrosterone, Am. J. Psychiatry, Apr. 1999: 646–649, 156:4.

F. Dhabhar, B. McEwen, Enhancing versus suppressive effects of stress hormones on skin immune function, Proc. Natl. Acad. Sci. USA. 6(Feb. 1999): 1059–1064, vol. 96.

P. Schultz, W. Schlotz, Trierer Inventar zur Erfassung von chronischem Streβ (TICS), , Diagnostica 45, Heft 1, Hogrefe Verlag Gottingen 1999: 8–19 (With English Abstract).

M. Horowitz, N. Wilner, W. Alvarez, Impact of Event Scale: A Measure of Subjective Stress, , Psychosomatic Medicine, (May 1979):209–218, vol. 41, No. 3.

P. Hunt, E. Gurnell, F. Huppert, C. Richards, A. Prevost, J. Wass, J. Herbert, V. Chatterjee, Improvement in Mood and Fatigue after Dehydroepiandrosterone Replacement in Addison's Disease in a Randomized, Double Blind Trial, The Journal of Clinical Endocrinology & Metabolism, 2000:4650–4656, vol. 85, No. 12.

M. Chren, R. Lasek, S. Flocke, S. Zyzanski, Improved Discriminative and Evaluative Capability of a Refined Version of Skindex, a Quality–of–Life Instrument for Patients with Skin Diseases, Arch Dermaology, Nov. 1997:1433–1440, vol. 133.

J. Kabat–Zinn, E. Wheeler, T. Light, A. Skillings, M. Scharf, T. Cropley, D. Hosmer, J Bernhard, Influence of a Mindfulness Meditation–Based Stress Reduction Intervention on Rates of Skin Clearing in Patients with Moderate to Severe Psoriasis Undergoing Phototherapy (UVB) and Photochemotherapy(PUVA), Psychosomatic Medicine (1998):625–632, vol. 60.

J. Kiecolt–Glaser, R. Glaser, E. Strain, J. Stout, K. Tarr, J. Holliday, C. Speicher, Modulation of Cellular Immunity in Medical Students, Journal of Behavioral Medicine, (1986):5–21., vol. 9, No. 1.

C. Chrousos, P. Gold, The Concepts of Stress and Stress System Disorders: Overview of Physical and Behaviorial Homeostasis, Stress and Stress Disorders–Chrousos & Gold, JAMA, Mar. 4, 1992:1244–1252, vol. 267, No. 9.

R. Sapolsky, Why Zebras Don't Get Ulcers, W. H. Freeman and Company, New York, 1998:1–18.

Tausk et al., Stress and the Skin, Arch Dermatol. Jan. 2001:78–82, vol. 137.

Scholzen, T., Armstrong, C.A., Bunnett, N.W., Luger, T. A., Olerud, J.E., Ansel, J.C., Neuropeptides in the skin: interactions between the neuroendocrine and the skin immune system, Experimental Dermatology, 1998:7:81–96, Denmark.

www.shiseldo.co. , publicly available prior to Dec. 7, 2001.

Bottle for Johnson's® Bedtime Bath™ (Oct. 1999).

Badia, P., et al., "Some Effects of Fragrances on Sleep" Compendium of Olfactory Research 1982–1994 ["Compendium"] 31–36 (1994).

Dember, William, et al., "Olfactory Stimulation and Sustained Attention" Compendium 39–46 (1994).

Saintigny, Gaelle, et al., "The use of Essential Oils to Stimulate the release of relaxing substances by human Ketatinocytes" XXIst IFSCC Int'l. Congress 2000, Berlin-Proceedings.

C. Kirschbaum and Dirk H. Hellhammer "Salivary Cortisol", Encyclopedia of Stress, vol. 3, pp 379–384.

Barbara Carlton, "In Quest for Prettiest Baby, Parents Snap up Pricey Kid's Cosmetics" Jun. 9, 2000, NewsEdge Insight ["Carlton"].

Karen Douthwaite "Bringing Up Baby", Oct. 1999.

Arthur A. Stone, Donald S. Cox, Heiddis Valdimarsdottir and Lina Jandorf, John M. Neale, "Evidence that Secretory IgA Antibody is Associated with Daily Mood" Journal of Personality and Social Psychology, 1987, vol. 52, No. 5, 9988–993.

Heim, Christine et. al. "The potential role of hypocortisolism is the pathophysiology of stress–related boldiy disorders". Psychoneurocrinology, vol. 25 No. 1, Jan. 2000 pp. 1–35 XP002239756.

Schmidt–Reinwald A. et. al , "The corisol response to awakening in relation to different challenge tests and a 12–hour cortisol rhythm" Life Sciences, vol. 64 No. 18, Mar. 26, 1999 pp. 1653–1660 XP002239757.

"Fussy Time" calming baby aromatherapy. Cited in Jun. 9, 2000 NewsEdge Article.

Friess, Elisabeth et. al. "The hypothalamic–pituitary–adrenocoritcal system and sleep in man", Advances in Neuroimmunology, vol. 5, pp. 111–125, 1995.

Leigh, Terry J. et. al, "Factor Analysis of the St. Mary's Hospital Sleep Questionnaire", Sleep 11(5), pp. 448–453, 1988.

Night Music 2 Classical Favourites for Relaxing and Dreaming—(1980) CD attached.

Kollias, N. et Al. "A single Parameter, Oxygenated Hemoglobin can be used to Quanitity Experimental Irritant–Induced Inflammation", The Journal of Investigative Dermatology, vol. 104, No. 3, pp 421–424, Mar. 1995.

Shaw, Christine R., "The perimenopausal Hot Flash: Epidemiology, Physiology, and Treatment", The Nurse Practitioner, vol. 22 No. 3, pp. 55–66, Mar. 1997.

Anarte, M.T., et Al. "Hormonal and psychological treatment: therapeutic alternative for menopausal women?" Maturitas, 29, PP. 203–213, 1998.

Aromatherapy Workbook, Marcel Lavabre, pp. 74,75,84, 104, 131–132,139,152 (1990).

Weil, Andrew, "Breathing–The Master Key to Self Healing" 2 CD Set (1999) CD's attached.

XP002208946 & WO 01 98442 A (Shiseido Co. Ltd), Dec. 27, 2001 abstract).

XP002208807 & JP 11 019076 (Pola Chem Ind. Inc.) Jan. 26, 1999 abstractt.

XP002208808 & JP 11 023579 (Pola Chem Ind. Inc.), Jan. 29, 1999 abstract.

Abstract JP 1185267 Geran Kaihatsu Kenk (1989) "Nasal Inhalation Instrument".

Abstract AU 9728425, Dobrincic, A (1998) "Soothing Calm Non Sting Herb Heal Strip . . . ".

N. Bolger, E. Schilling, Personality and the Problems of Everyday Life: The Role of Neuroticism in Exposure and Reactivity to Daily Stressors, Journal of Personality, Sep. 1991: 355–386, 59:3.

M. Sutzberger, S. Zaidens,Psychogenic Factors in Dermatologic Disorders, 1948:669–685.

A. Garg, M. Chren, L. Sands, M. Matsui, K. Marenus, K. Feingold, P. Elias, Psychological Stress Perturbs Epidermal Permeability Barrier Homeostasis, Implications for the Pathogenesis of Stress–Assoicated Skin Disorders, Arch Dermatol, (Jan. 2001)53–59., vol. 137.

E. Panconsesi, G. Hautmann, Psychophysiology of Stress in Dermatology: The Psychobiologic Pattern of Psychomatics, Dermatologic Clinics, (Jul. 1996): 399–421., vol. 15, No. 3.

C. Kirschbaum, D. Hellhammer, Salivary Cortisol in Psychobiological Research: An Overview, Neuropsychobiology 1989:150–169, vol. 22.

C. Kirschbaum, D. Hellhammer, Salivary Cortisol in Psychoneuroendocrine Research: Recent Developments and Applicantions, Psychoneuroendocrinology, 1994, 313–333, vol. 19, No. 4.

M. Denda, T. Tsuchiya, P. Elias, K. Feingold, Stress alters cutaneous permeability barrier homeostatis, Am. J. Physiol. Regulatory Integrative Comp. Physiol., 2000:R367–R372., Vo. 278.

R. A. Dressendorfer, C. Kirschbaum, W. Rohde, F. Stahl, C.J. Strasburger, Synthesis of a Cortisol–Biotin Conjugate and Evaluation as a Tracer in an Immunoassay for Salivary Cortisol Measurement, J. Steroid Biochem, Molec. Biol. 1992, 683–692, vol. 43, No. 7.

A, Delongis, S. Folkman, R. Lazarus, The Impact of Daily Stress on Health and Mood:Psychological and Social Resources as Mediators, Journal of Personality and Social Psychology, 1988:486–495, vol. 54, No. 3.

* cited by examiner

METHOD OF MEASURING THE STRESS OR RELAXATION LEVEL OF A MAMMAL

CLAIM OF PRIORITY

This application claims priority to Great Britain Patent Application No. 0202032.9 filed Jan. 29, 2002.

FIELD OF THE INVENTION

This invention is related to methods of measuring and changing the level of stress or relaxation level in mammals. More particularly, the invention is related to methods of measuring and changing the activity of the sympathetic nervous system of a mammal.

BACKGROUND OF THE INVENTION

Advances in technology in the last century have brought benefits to society but have resulted in a greater prevalence of stress in the daily lives of people at all levels of society. Our stress response mechanisms have not adapted at the same pace as advancing technology. The effect of stress on health and well being is well documented. See, for example, Robert M. Sapolsky, *Why Zebra's Don't Get Ulcers-An Updated Guide to Stress, Stress Related Diseases and Coping*, ISBN 0-7167-3210-6, Chapter 1, (5th Edition 2000), and George P. Chrousos and Philip W. Gold, "The Concepts of Stress and Stress System Disorders-Overview of Physical and Behavioral Homeostasis," *JAMA*, Mar. 4, 1992, Vol. 267, No. 9. It is known that stress, particularly chronic stress, may cause or aggravate many conditions, including immunosuppression and susceptibility to infectious diseases, gastric conditions, sleep problems, depression, premature birth in expectant mothers, low birth weight, degeneration of brain neurons leading to memory and learning problems, elevated blood pressure, heart complications and stroke due to elevated blood lipid levels and other health complications.

Repeated exposure to acute stressors may lead to chronic stress. The acute stress response is commonly known as the "fight or flight" response. Acute stress is any stimulus or experience that is perceived as causing conflict or danger. In modern life, there exists a multitude of sources of acute stress, some examples of which include stress associated with interviews, public speaking, examinations, a dispute within a relationship, a traffic jam, being told some unpleasant news, or witnessing an unpleasant or disturbing scene. The "fight or flight" response promotes survival by protecting from bodily harm through providing the physical resources required either for conflict with the danger (fight) or to escape from the danger (flight). The response originates in the hypothalamus, which responds to a stressor by activating the sympathetic nerve endings in the adrenal medulla to produce epinephrine (adrenaline) as a part of the sympathetic-adrenal-medulla (SAM) system. Epinephrine (adrenaline) is secreted by the nerve endings in the adrenal medulla and norepinephrine (noradrenaline) is secreted by all other sympathetic nerve endings in the body that control relatively unconscious functions, including heart rate, digestion and salivary flow. It is epinephrine and norepinephrine that produce the "fight or flight" response in the organs of the body, preparing the mammal to respond to a stressor by increasing heart rate, increasing blood flow to muscles, diverting blood flow from the digestive system and inhibiting digestion, inhibiting saliva flow and dilating pupils, which are all desirable physiological responses in a survival threatening situation.

One method of measuring the response to an acute stressor in a mammal is to monitor the hypothalamus-pituitary-adrenal (HPA) system, and, in particular, the release of cortisol, corticotropin releasing hormone (CRH) and adrenocorticotrophic hormone (ACTH). Cortisol may be detected in saliva as a measure of response to a stressor. However, where cortisol is secreted in response to an acute stressor, it takes approximately twenty minutes after the onset of the stressor before the change in cortisol is detectable in saliva. Furthermore, additional time is required for the quantitative analysis of cortisol in saliva.

Given that the rapid onset of an acute stress response, or conversely the immediate physiological response to relaxation, occurs over a short time frame (generally on the order of seconds), measurement of changes of bodily functions controlled by the sympathetic nervous system would be useful in measuring stress or relaxation response. Accordingly, there remains a need for a time-independent measure of the acute stress or acute relaxation response of a mammal.

Another method of measuring the response to stress or relaxation is to quantify or observe physiological changes driven by the sympathetic nervous system. For example, some devices like mood rings and thumb press stress indicators, which rely on skin temperature changes, are simple however they only measure qualitative temperature differences. Other techniques, including lie detector type tests, such as those described in Japanese Kokai 11-034688, which rely on skin impedance changes, and thermal imaging techniques, such as those described in U.S. Pat. No. 5,771, 261, which rely on skin temperature changes, may be used to supply quantitative information on the response to stress or relaxation, but these techniques are complicated and cumbersome.

Given the shortcomings of known methodology, there exists a need for a non-invasive, easy-to-use, time-independent and non-cumbersome method of measuring the state of the sympathetic nervous system as a means of measuring acute stress or relaxation response in a mammal.

The present invention addresses the problem of quantitatively measuring the immediate physiological response to acute stress or relaxation in a non-invasive, time-independent and easy-to-use method. We have surprisingly found that comparisons of the levels of oxyhemoglobin and deoxyhemoglobin in cutaneous blood supply provide a quantitative measure and a means of monitoring the acute stress or relaxation level of a mammal.

SUMMARY OF THE INVENTION

In one embodiment, the invention is directed to a method of measuring the stress or relaxation level of a mammal, including the step of:

measuring the ratio of the level of deoxyhemoglobin to the level of oxyhemoglobin of the mammal [$Hb/HbO_2$]; or measuring the ratio of the level of deoxyhemoglobin to the sum of the level of deoxyhemoglobin and the level of oxyhemoglobin of the mammal [$Hb/(Hb+HbO_2)$].

In another embodiment, the invention is directed to a method of measuring the activity of the sympathetic nervous system of a mammal, including the step of:

measuring the ratio of the level of deoxyhemoglobin to the level of oxyhemoglobin of the mammal [$Hb/HbO_2$]; or measuring the ratio of the level of deoxyhemoglobin to the sum of the level of deoxyhemoglobin and the level of oxyhemoglobin of the mammal [$Hb/(Hb+HbO_2)$].

In another embodiment, the invention is directed to a method of measuring the activity of the sympathetic nervous system of a mammal, including the steps of:

a. measuring the level of oxyhemoglobin and the level of deoxyhemoglobin in the cutaneous blood supply of the mammal prior to exposing said mammal to an acute stressor or relaxor;
b. exposing the mammal to the acute stressor or relaxor;
c. measuring the level of oxyhemoglobin and the level of deoxyhemoglobin in the cutaneous blood supply of the mammal during or after the exposing step; and
d. for step a and step c, calculating and comparing at least one ratio selected from the group consisting of:
   i. the ratio of the level of deoxyhemoglobin to the level of oxyhemoglobin of said mammal; and
   ii. the ratio of the level of deoxyhemoglobin to the sum of the level of deoxyhemoglobin and the level of oxyhemoglobin of said mammal. Preferably, the level of deoxyhemoglobin and oxyhemoglobin are measured by at least one noninvasive technique, including spectroscopic techniques, such as diffuse reflectance spectroscopy, near infrared spectroscopy or ultraviolet-visible spectroscopy.

In yet another embodiment, the invention is directed to a method of changing the activity of the sympathetic nervous system of a mammal, including the steps of:

a. measuring the level of oxyhemoglobin and the level of deoxyhemoglobin in the cutaneous blood supply of the mammal prior to exposing the mammal to an acute stressor or relaxor;
b. exposing the mammal to the acute stressor or relaxor;
c. measuring the level of oxyhemoglobin and the level of deoxyhemoglobin in the cutaneous blood supply of the mammal during or after the exposing step;
d. for step a and step c, calculating and comparing at least one ratio selected from the group consisting of:
   i. the ratio of the level of deoxyhemoglobin to the level of oxyhemoglobin of the mammal; and
   ii. the ratio of the level of deoxyhemoglobin to the sum of the level of deoxyhemoglobin and the level of oxyhemoglobin of the mammal; and
e. changing at least one of the ratios before and after step b by at least 1%, preferably at least 5% and most preferably at least 10%. Preferably, the changing step e includes the step of administering an effective amount of sensory regimen to the mammal. Examples of a suitable sensory regimen include the administration of sensory stimuli selected from auditory stimuli, visual stimuli, tactile stimuli, gustatory stimuli and olfactory stimuli and combinations thereof.

In one particularly preferred embodiment, the mammal is a human operator of a vehicle or a machine and the method preferably includes the step of alerting the human operator of impaired ability to operate the vehicle or the machine, caused by stress, agitation, exhaustion, sleepiness, inattentiveness, boredom, illness and distraction. Most preferably, the method further includes the step of administering an effective amount of sensory regimen.

In a particularly preferred embodiment, the mammal is a human operator of a vehicle or a machine and the method preferably includes the step of alerting the mammal of a detrimental level of stress, such as the stress caused by heavy traffic or dangerous situations leading so-called "road rage." Most preferably, the method further includes the step of administering an effective amount of sensory regimen.

In another particularly preferred embodiment, the mammal suffers from cardiovascular disease or related complications and the method preferably includes the step of alerting the mammal of a detrimental level of stress. Most preferably, the method further includes the step of administering an effective amount of sensory regimen.

In yet another particularly preferred embodiment, the mammal is pregnant and the method preferably includes the step of alerting the pregnant mammal of a detrimental level of stress. Most preferably, the method further includes the step of administering an effective amount of sensory regimen.

In another particularly preferred embodiment, the mammal is preparing for sleep and the method preferably includes the step of alerting the mammal of a detrimental level of stress. Most preferably, the method further includes the step of administering an effective amount of sensory regimen.

The mammal may alerted to a detrimental level of stress in any of a number of ways that includes feedback to the mammal when such level is approached or exceeding, such as a visual indication (for example, flashing or colored lights), audio indication (for example, voice message, beeping sound or alarm), tactile indication (for example, vibration or mild shock) or combinations thereof.

In a particularly preferred embodiment, the invention is directed to a method of improving the complexion of the skin of a mammal, including the steps of:

a. measuring the level of oxyhemoglobin and the level of deoxyhemoglobin in the cutaneous blood supply of the mammal prior to exposing the mammal to an acute relaxor;
b. exposing the mammal to the acute relaxor;
c. measuring the level of oxyhemoglobin and the level of deoxyhemoglobin in the cutaneous blood supply of the mammal during or after the exposing step;
d. for step a and step c, calculating and comparing at least one ratio selected from the group consisting of:
   i. the ratio of the level of deoxyhemoglobin to the level of oxyhemoglobin of the mammal; and
   ii. the ratio of the level of deoxyhemoglobin to the sum of the level of deoxyhemoglobin and the level of oxyhemoglobin of the mammal; and
e. reducing at least one of the ratios before and after step b by at least 1%, preferably at least 5% and most preferably at least 10%.

Preferably, the changing step e includes the step of administering an effective amount of sensory regimen to the mammal.

DETAILED DESCRIPTION OF THE INVENTION

As discussed above, the techniques according to the invention provide methods in which the level of acute stress or acute relaxation of a mammal may be non-invasively and easily measured quantitatively during or immediately following a stressful or relaxing experience.

As used herein, the term "mammals" includes any of a class of warm-blooded higher vertebrates that nourish their young with milk secreted by mammary glands and have skin usually more or less covered with hair, and non-exclusively includes humans, dogs and cats.

As used herein, the term "acute stressor" or "acute stress" is any stimulus or experience that is perceived by the mammal as either a source of conflict or danger.

As used herein, the term "acute relaxor" or "acute relaxation" is any stimulus or experience that is perceived by the mammal as a source of relaxation.

Techniques that quantify the level of saturation of oxygen in the blood and that may be used to compare the levels of oxyhemoglobin ($HbO_2$) to deoxyhemoglobin (Hb) in cutaneous blood supply are useful in the practice of the invention. Specifically, the techniques that may be used in the practice of the methods of the invention are techniques that measure the intensity of transmitted or reflected electromagnetic waves respectively through or from the cutaneous tissue of a mammal, including diffuse reflectance spectroscopy (DRS), near infrared spectroscopy (NIR) and ultraviolet-visible (UV-vis) spectroscopy. Use of these techniques gives values of oxyhemoglobin and deoxyhemoglobin in arbitrary units that may subsequently be used in the calculation of the ratios [$Hb/(Hb+HbO_2)$ and $Hb/HbO_2$].

Since cutaneous blood flow will vary from individual to individual, one must first select an appropriate baseline measurement. As an example, an occasion could be chosen, because the individual is "stress" free, such as, for example, after a restful experience. In this case, one is using this invention to measure any increases in stress in the individual. On the other hand, the initial occasion could be representative of a time where the individual has some level of detrimental stress. In this case, subsequent measures can be used to determine the amount and effectiveness of a stress management or intervention technique.

Once the ratio(s) has been calculated, a comparison may be done between the ratio(s) after exposure to the stressor or relaxor and the baseline ratio(s) prior to the exposure to the stressor or relaxor, to determine the change, if any, in stress or relaxation level of the mammal from the baseline measurement to the current testing interval. A comparison of all of these values is necessary to help determine the magnitude of the effect.

The level of $HbO_2$ and Hb are measured during or after the exposing the mammal to the stressor or relaxor. If analysis of the current state of the sympathetic nervous system of the mammal is desired, it is preferable to measure the levels of $HbO_2$ and Hb either during the exposure of the stressor or relaxor or immediately following the exposure, generally within 15 minutes, preferably 5 minutes and more preferably 1 minute. However, long periods of time are contemplated within the scope of this invention.

The methods of the invention may be used to monitor the stress or relaxation level of a mammal, and where appropriate administer a treatment to either reduce or increase the activity of the sympathetic nervous system of the mammal to effect relaxation or stimulation. In cases where it is desired to change the activity of the sympathetic nervous system of a mammal, a step of administering a sensory regimen is included. For example, when a difference between the subsequent measure of activity of the sympathetic nervous system (after exposure to the stressor or relaxor) and the baseline stress value (prior to the exposure to the stressor or relaxor) of at least 1%, at least 5%, and at least 10% different is desired, the method of the invention may preferably include an additional step wherein the activity of the sympathetic nervous system system is changed to at least original baseline level or lower in the case where a reduction in stress level is desired, or, alternatively, to at least some set goal level in the case where an increase in the stimulation level is desired.

Examples of a suitable sensory regimen include the administration of sensory stimuli selected from auditory stimuli, visual stimuli, tactile stimuli, gustatory stimuli and olfactory stimuli and combinations thereof.

As used herein, "effective amount" refers to the frequency, level and duration of the regime of sensory experience sufficient to significantly induce a positive modification in the condition to be treated, but low enough to avoid serious side effects (at a reasonable benefit/risk ratio), within the scope of sound medical judgment. The effective amount of the compound or composition will vary with the particular condition being treated, the age and physical condition of the patient being treated, the severity of the condition, the frequency, level and duration of the treatment, the nature of concurrent therapy, the specific compound or composition employed, the particular pharmaceutically-acceptable carrier utilized, and like factors within the knowledge and expertise of the attending physician. Use of a multiple sensory regimen can affect the duration that would be needed to create the desired response.

Examples of desired responses when relaxation is sought include:
(i) a reduction in the ratio of deoxyhemoglobin to the sum of deoxyhemoglobin and oxyhemoglobin ($Hb/(Hb+HbO_2)$) in the cutaneous blood supply of the mammal;
(ii) a reduction in the ratio of deoxyhemoglobin to oxyhemoglobin ($Hb/HbO_2$) in the cutaneous blood supply of the mammal; or
(iii) both (i) and (ii).

Examples of desired responses when stimulation is sought include:
(i) an increase in the ratio of deoxyhemoglobin to the sum of deoxyhemoglobin and oxyhemoglobin ($Hb/(Hb+HbO_2)$) in the cutaneous blood supply of said mammal;
(ii) an increase in the ratio of deoxyhemoglobin to oxyhemoglobin ($Hb/HbO_2$) in the cutaneous blood supply of the mammal; or
(iii) both (i) and (ii).

A preferred means of delivering sensory stimuli is in the form of a personal care composition. Personal care compositions are particularly useful in delivering olfactory stimuli. For example, the sensory fragrance may be produced by mixing the selected essential oils and odoriferous components under ambient conditions until the final mixture is homogenous using equipment and methodology commonly known in the art of fragrance compounding. It is preferable to store the final sensory fragrance mixture under ambient conditions for a few hours after mixing before using it as a component of a personal care composition.

The personal care compositions useful in the methods of the present invention may then be produced by blending the desired components with the sensory fragrance using equipment and methodology commonly known in the art of personal care product manufacture. To improve the solubilization of the sensory fragrance in aqueous personal care compositions, the sensory fragrance may be pre-blended with one or more of the nonionic surfactants.

"Personal care compositions" refers to personal cosmetic, toiletry, and healthcare products such as dry and wet wipes, washes, baths, shampoos, gels, soaps, sticks, balms, sachets, pillows, mousses, sprays, lotions, creams, cleansing compositions, powders, oils, bath oils and other bath compositions which may be added to a bath. Personal care compositions may also include, but are not limited to, aerosols, candles, and substances that may be used with vaporizers. The aforementioned wipes, washes, baths, shampoos, gels, soaps, sticks, balms, sachets, pillows, mousses, sprays, lotions, creams, cleansing compositions, oils, and bath oils, are commercially known to those who have knowledge of preparing personal care compositions. Suitable personal care compositions, include but are not limited to Johnson's Bedtime Bath® product available from Johnson & Johnson Consumer Companies, Inc.

To achieve the desired response in a mammal, the personal care composition may be used in a dosing amount that is in accordance with the prescribed directions of the personal care composition. Although a greater effect is generally achieved when multiple stimuli are used together, a single stimulus may also be effective so are included in the invention.

Practice of a sensory regimen using the aforementioned stimuli may lead to acute relaxation and increased levels of oxygenated hemoglobin cutaneous blood supply. Accordingly, another embodiment of the invention is a method of increasing the supply of blood-borne nutrients, including oxygen, to cutaneous tissue of a mammal by administering to the mammal an effective amount of a sensory regimen. When the supply to cutaneous tissue of blood-borne nutrients, including oxygen, is enhanced, good health of the tissue is promoted. There are several technical methods of measuring the state of health of the skin, including transepidermal water loss, pH, and type and count of microflora. A visual indicator that would be meaningful to the consumer is a healthy complexion. By the term "healthy complexion" is meant skin that has even skin tone, is free of blemishes and is glowing and radiant. Accordingly, the methods of the invention may be used to improve the complexion of the skin of a mammal.

To illustrate the methods of the invention, the following examples are included. These examples do not limit the invention. They are meant only to describe a method of practicing the invention.

EXAMPLES

Example 1

One Time Exposure to Audio Stimuli and Short Term Effect on Sympathetic Nervous System Activity As Measured By $HbO_2$ and Hb Levels in Cutaneous Blood Supply Using Diffuse Reflectance Spectroscopy A group of males and females aged 20 to 55 in good general health were invited to participate in a paid study in which over the course of 10 minutes they would listen to soothing sounds. The purpose of this study was to measure the effect of the experience on sympathetic nervous system activity as measured by deoxyhemoglobin (Hb) and oxyhemoglobin ($HbO_2$) levels in cutaneous blood supply using diffuse reflectance spectroscopy (DRS) in the time period following the application of a positive stressor (relaxing music).

The diffuse reflectance spectroscopic technique used to quantify and analyze spectra for Hb and $HbO_2$ levels is described in detail by N. Kollias et al. in "A Single Parameter, Oxygenated Hemoglobin, Can Be Used to Quantify Experimental Irritant-Induced Inflammation," *The Journal of Investigative Dermatology*, Vol. 104, No 103, March 1995, and is incorporated herein by reference.

Upon arriving at the study site, the panelist was asked to sit quietly for 10 minutes and relax. Three baseline DRS measurements were performed on the volar forearm of the panelist. The panelist then listened to 10 minutes of relaxing music from the music CD entitled "Relax with Ocean Relaxing Surf" by Eclipse Music Group Ocean Wave Music through personal headphones. During or immediately following this 10-minute session, three DRS measurements were performed on the same area of the volar forearm as was used for the baseline measurements. The data was then transferred into a program that presented the DRS data in an ASCII file format. The results of the spectroscopic analyses are presented in Table 1 below.

TABLE 1

| Panelist | $HbO_2$ Before (Arbitrary Units) | $HbO_2$ After (Arbitrary Units) | Hb Before (Arbitrary Units) | Hb After (Arbitrary Units) |
|---|---|---|---|---|
| 1 | 0.30 | 0.31 | 0.61 | 0.31 |
| 2 | 0.25 | 0.25 | 0.57 | 0.46 |
| 3 | 0.14 | 0.18 | 0.39 | 0.31 |
| 4 | 0.26 | 0.34 | 0.81 | 0.32 |
| 5 | 0.14 | 0.17 | 0.49 | 0.39 |
| 6 | 0.22 | 0.23 | 0.49 | 0.28 |
| 7 | 0.20 | 0.25 | 0.50 | 0.44 |
| 8 | 0.28 | 0.32 | 0.78 | 0.32 |
| 9 | 0.18 | 0.10 | 0.67 | 0.26 |
| 10 | 0.26 | 0.27 | 0.66 | 0.09 |
| 11 | 0.22 | 0.24 | 0.54 | 0.46 |
| 12 | 0.33 | 0.51 | 0.87 | 0.09 |
| Average | 0.23 | 0.26 | 0.62 | 0.31 |

The ratio of $Hb/(Hb+HbO_2)$ and the ratio of $Hb/HbO_2$ were subsequently calculated from the average values of Hb and $HbO_2$ presented in Table 1. The result of these calculations are shown in Table 2 below:

TABLE 2

|  | $Hb/(Hb + HbO_2)$ | $Hb/HbO_2$ |
|---|---|---|
| Before Stressor | 0.73 | 2.70 |
| After Stressor | 0.54 | 1.19 |

The ratio of $Hb/(Hb+HbO_2)$ and the ratio of $Hb/HbO_2$ decreased following the application of the positive stressor. A decrease in these ratios indicates increased cutaneous supply of oxygenated blood, which would be consistent with an acute relaxation response.

Example 2

One Time Exposure to Arithmetic Challenge and Short Term Effect on Sympathetic Nervous System Activity as Measured By $HbO_2$ and Hb levels in Cutaneous Blood Supply Using Diffuse Reflectance Spectroscopy A group of males and females aged 20 to 55 in good general health were invited to participate in a paid study in which over the course of 10 minutes they were given a series of arithmetic problems to solve, the experience of which was subjectively perceived to be stressful. The purpose of this study was to measure the effect of the experience on sympathetic nervous system activity as measured by deoxyhemoglobin (Hb) and oxyhemoglobin ($HbO_2$) levels in cutaneous blood supply using diffuse reflectance spectroscopy in the time period following the application of the negative stressor.

Baseline measures of Hb and $HbO_2$ were made using diffuse reflectance spectroscopy as set forth in Example 1. Each adult was then asked to provide the correct answers to a series of arithmetic questions within a period of 10 minutes. Immediately following this arithmetic challenge a second measurement of Hb and $HbO_2$ was made for each panelist as set forth in Example 1. The results of the spectroscopic analyses are presented in Table 3 below.

TABLE 3

| Panelist | HbO₂ Before (Arbitrary Units) | HbO₂ After (Arbitrary Units) | Hb Before (Arbitrary Units) | Hb After (Arbitrary Units) |
|---|---|---|---|---|
| 1 | 0.17 | 0.20 | 0.43 | 0.51 |
| 2 | 0.24 | 0.29 | 0.58 | 0.62 |
| 3 | 0.13 | 0.10 | 0.46 | 0.48 |
| 4 | 0.32 | 0.20 | 0.64 | 0.92 |
| 5 | 0.12 | 0.15 | 0.49 | 0.52 |
| 6 | 0.15 | 0.19 | 0.61 | 0.47 |
| 7 | 0.22 | 0.18 | 0.58 | 0.42 |
| 8 | 0.21 | 0.25 | 0.75 | 0.82 |
| 9 | 0.22 | 0.19 | 0.83 | 0.93 |
| 10 | 0.19 | 0.17 | 0.63 | 0.56 |
| 11 | 0.16 | 0.16 | 0.54 | 0.57 |
| 12 | 0.25 | 0.39 | 0.66 | 0.93 |
| Average | 0.20 | 0.20 | 0.60 | 0.65 |

The ratio of $Hb/(Hb+HbO_2)$ and ratio of $Hb/HbO_2$ were subsequently calculated from the average values of Hb and $HbO_2$ presented in Table 3. The result of this calculation is shown in Table 4 below:

TABLE 4

|  | $Hb/(Hb + HbO_2)$ | $Hb/HbO_2$ |
|---|---|---|
| Before | 0.75 | 3.0 |
| After | 0.76 | 3.25 |

The ratio of $Hb/(Hb+HbO_2)$ and ratio of $Hb/HbO_2$ increased following the arithmetic challenge. An increase in these ratios indicates decreased cutaneous supply of oxygenated blood that would be indicative of redirection of oxygen away from cutaneous tissue and towards tissues and organs that would be involved in a flight or flight response to a challenge. The magnitude of the increase here is somewhat limited, but it would be expected that in the face of a real, rather than an artificial challenge, that the magnitude of the increase would be greater. In a laboratory setting ethics necessarily prohibits the nature of the stressor, thus the usefulness of this method in the measurement of an acute stress response is not best demonstrated under the conditions described in this example.

We claim:

1. A method of measuring the stress or relaxation level of a mammal, comprising the step of:
   a. measuring the level of oxyhemoglobin and the level of deoxyhemoglobin in the cutaneous blood supply of said mammal prior to exposing said mammal to an acute stressor or relaxor;
   b. exposing said mammal to said acute stressor or relaxor;
   c. measuring the level of oxyhemoglobin and the level of deoxyhemoglobin in the cutaneous blood supply of said mammal during or after said exposing step; and
   d. for step a and step c, calculating and comparing at least one ratio selected from the group consisting of:
      i. the ratio of the level of deoxyhemoglobin to the level of oxyhemoglobin of said mammal; and
      ii. the ratio of the level of deoxyhemoglobin to the sum of the level of deoxyhemoglobin and the level of oxyhemoglobin of said mammal.

2. A method of measuring the activity of the sympathetic nervous system of a mammal, comprising the steps of:
   a. measuring the level of oxyhemoglobin and the level of deoxyhemoglobin in the cutaneous blood supply of said mammal prior to exposing said mammal to an acute stressor or relaxor;
   b. exposing said mammal to said acute stressor or relaxor;
   c. measuring the level of oxyhemoglobin and the level of deoxyhemoglobin in the cutaneous blood supply of said mammal during or after said exposing step; and
   d. for step a and step c, calculating and comparing at least one ratio selected from the group consisting of:
      i. the ratio of the level of deoxyhemoglobin to the level of oxyhemoglobin of said mammal; and
      ii. the ratio of the level of deoxyhemoglobin to the sum of the level of deoxyhemoglobin and the level of oxyhemoglobin of said mammal.

3. The method of claim 1 or 2, wherein said level of deoxyhemoglobin and said level of oxyhemoglobin are measured by at least one noninvasive technique.

4. The method of claim 3, wherein said technique is spectroscopy.

5. The method of claim 4, wherein said spectroscopy is at least one technique selected from the group consisting of diffuse reflectance spectroscopy, near infrared spectroscopy and ultraviolet-visible spectroscopy.

6. A method of changing the stress or relaxation level of a mammal, comprising the steps of:
   a. measuring the level of oxyhemoglobin and the level of deoxyhemoglobin in the cutaneous blood supply of said mammal prior to exposing said mammal to an acute stressor or relaxor;
   b. exposing said mammal to said acute stressor or relaxor;
   c. measuring the level of oxyhemoglobin and the level of deoxyhemoglobin in the cutaneous blood supply of said mammal during or after said exposing step;
   d. for step a and step c, calculating and comparing at least one ratio selected from the group consisting of:
      i. the ratio of the level of deoxyhemoglobin to the level of oxyhemoglobin of said mammal; and
      ii. the ratio of the level of deoxyhemoglobin to the sum of the level of deoxyhemoglobin and the level of oxyhemoglobin of said mammal; and
   e. changing at least one of said ratios before and after step b by at least 1% by administering an effective amount of a sensory regimen.

7. A method of changing the activity of the sympathetic nervous system of a mammal, comprising the steps of:
   a. measuring the level of oxyhemoglobin and the level of deoxyhemoglobin in the cutaneous blood supply of said mammal prior to exposing said mammal to an acute stressor or relaxor;
   b. exposing said mammal to said acute stressor or relaxor;
   c. measuring the level of oxyhemoglobin and the level of deoxyhemoglobin in the cutaneous blood supply of said mammal during or after said exposing step;
   d. for step a and step c, calculating and comparing at least one ratio selected from the group consisting of:
      i. the ratio of the level of deoxyhemoglobin to the level of oxyhemoglobin of said mammal; and
      ii. the ratio of the level of deoxyhemoglobin to the sum of the level of deoxyhemoglobin and the level of oxyhemoglobin of said mammal; and
   e. changing at least one of said ratios before and after step b by at least 1% by administerinig an effective amount of a sensory regimen.

8. The method of claim 6 or claim 7, wherein at least one of said ratios before and after step b is changed by at least 5%.

9. The method of claim 6 or claim 7, wherein at least one of said ratios before and after step b is changed by at least 10%.

10. The method of claim 6 or claim 7, wherein said changing step e is a reduction.

11. The method of claim 6 or claim 7, wherein said changing step e is an increase.

12. The method of claim 6 or claim 7, wherein said mammal is a human operator of a vehicle or a machine.

13. The method of claim 12, further comprising the step of:

alerting said human operator of impaired ability to operate said vehicle or said machine.

14. The method of claim 6 or claim 7, wherein said mammal has cardiovascular disease or related complications.

15. The method of claim 6 or claim 7, wherein said mammal is pregnant.

16. The method of claim 6 or claim 7, wherein said mammal is preparing for sleep.

17. The method of claim 6 or claim 7, further comprising the step of:

alerting said mammal of a detrimental level of stress.

18. A method of improving the complexion of the skin of a mammal, comprising the steps of:

a. measuring the level of oxyhemoglobin and the level of deoxyhemoglobin in the cutaneous blood supply of said mammal prior to exposing said mammal to an acute relaxor;

b. exposing said mammal to said acute relaxor;

c. measuring the level of oxyhemoglobin and the level of deoxyhemoglobin in the cutaneous blood supply of said mammal during or after said exposing step;

d. for step a and step c, calculating and comparing at least one ratio selected from the group consisting of:

i. the ratio of the level of deoxyhemoglobin to the level of oxyhemoglobin of said mammal; and ii. the ratio of the level of deoxyhemoglobin to the sum of the level of deoxyhemoglobin and the level of oxyhemoglobin of said mammal; and e. reducing at least one of said ratios before and after step b by at least 1% by administering an effective amount of a sensory regimen wherein said effective amount is effective to improve the complexion of the skin of said mammal.

19. The method of claim 18, wherein at least one of said ratios before and after step b is reduced by at least 5%.

20. The method of claim 19, wherein at least one of said ratios before and after step b is reduced by at least 10%.

* * * * *